(12) United States Patent
Tien et al.

(10) Patent No.: US 8,809,581 B2
(45) Date of Patent: Aug. 19, 2014

(54) METHOD OF MAKING 6-AMINOCAPROIC ACID AS ACTIVE PHARMACEUTICAL INGREDIENT

(71) Applicant: Sunny pharmtech Inc., Taoyuan County (TW)

(72) Inventors: Jien-Heh Tien, Hayward, CA (US); Chu-yi Pang, Taipei (TW)

(73) Assignee: Sunny Pharmtech Inc., Taoyuan County (TW)

( * ) Notice: Subject to any disclaimer, the term of this patent is extended or adjusted under 35 U.S.C. 154(b) by 0 days.

(21) Appl. No.: 13/660,126

(22) Filed: Oct. 25, 2012

(65) Prior Publication Data

US 2014/0039219 A1 Feb. 6, 2014

(30) Foreign Application Priority Data

Aug. 3, 2012 (TW) ............................. 101128069 A

(51) Int. Cl.
  *C07C 205/00* (2006.01)
(52) U.S. Cl.
  USPC ........................................................ 562/553

(58) Field of Classification Search
  CPC ................................................... C07C 227/22
  See application file for complete search history.

(56) References Cited

U.S. PATENT DOCUMENTS

| | | | | |
|---|---|---|---|---|
| 3,113,966 A | * | 12/1963 | Formaini et al. | 562/553 |
| 3,655,748 A | * | 4/1972 | Tandara | 562/553 |
| 2011/0152573 A1 | * | 6/2011 | Saigoku et al. | 562/507 |

* cited by examiner

*Primary Examiner* — Karl J Puttlitz
(74) *Attorney, Agent, or Firm* — WPAT, PC; Justin King

(57) ABSTRACT

The present invention provides a method for making 6-aminocaproic acid as an active pharmaceutical ingredient. The method comprises: performing a hydrolysis procedure to have ε-caprolactam react with acid or base to generate a first reaction mixture, performing a modification procedure to have a solubility regulating agent reacts with 6-aminocaproic acid in the first reaction mixture to form a second reaction mixture including an aminocaproic acid intermediate, performing a separation procedure to have the intermediate separated from the second reaction mixture and performing a hydrogenation procedure to have the aminocaproic acid intermediate hydrogenated to form a 6-aminocaproic acid product.

8 Claims, No Drawings

METHOD OF MAKING 6-AMINOCAPROIC ACID AS ACTIVE PHARMACEUTICAL INGREDIENT

BACKGROUND OF THE INVENTION

1. Field of the Invention

The present invention is generally related to a method of making 6-aminocaproic acid, and more particularly to a method of making 6-aminocaproic acid as an active pharmaceutical ingredient.

2. Description of the Prior Art

At present, various methods of making 6-aminocaproic acid are known and established because of its extensive applications. 6-aminocaproic acid is used in industry as a starting material for polymerizing ϵ-caprolactam to form Nylon-6 while medically it can be used to treat bleeding. However, 6-aminocaproic acid as an active pharmaceutical ingredient requires properties such as low ash content (i.e. low salt content or low residue on ignition), low heavy metal content, low water content, and no foul odor in addition to high purity. Besides, the processes of making 6-aminocaproic acid also require no involvement of toxic materials.

The method of making 6-aminocaproic acid, according to the prior art, includes the methods disclosed in Organic Syntheses, Coll. Vol. 4, p. 39 (1963) and Vol. 32, p. 13 (1952) where ϵ-caprolactam was hydrolyzed and then purified by column chromatography using Amberlite resin. However, the purification by ion exchange resin causes the product containment with colored impurity and odor. This method usually used to produce small amount of products and associated with high cost. It is not practical to use in large scale production.

On the other hand, U.S. Pat. No. 3,655,748 disclosed a method of making 6-aminocaproic acid from ϵ-caprolactam. Although it was reported that the produced 6-aminocaproic acid was obtained with low ash content, the process includes mixing ϵ-caprolactam with barium hydroxide, hydrolyzing ϵ-caprolactam to produce 6-aminocaproic acid, adding $CO_2$ gas to form precipitates of barium carbonate to obtain free acid of 6-aminocaproic acid. However, barium carbonate is toxic and is not suitable for the active pharmaceutical ingredient application.

The other methods, for example, reported in U.S. Pat. No. 4,950,429, U.S. Pat. No. 6,452,002, U.S. Pat. No. 6,372,939, for making 6-aminocaproic acid are mostly applied to Nylon-6 production and have problems for the active pharmaceutical ingredient application, such as complicate processing, expensive reagents, toxic intermediates, and high ash content.

Therefore, a novel method of making 6-aminocaproic acid (or ϵ-aminocaproic acid) as an active pharmaceutical ingredient is urgently needed to produce high quality product to meet medical requirements.

SUMMARY OF THE INVENTION

In accordance with the present invention, a method of making 6-aminocaproic acid is provided. The method uses a low-cost starting material (ϵ-caprolactam) without using column chromatography in purification and has simple process to be able to massively produce 6-aminocaproic acid to meet the requirements as an active pharmaceutical ingredient.

One object of the present invention is to provide a method to make 6-aminocaproic acid which comprises: performing a hydrolysis procedure to have ϵ-caprolactam react with acid or base to generate a first reaction mixture, performing a modification procedure to have a solubility regulating agent react with 6-aminocaproic acid in the first reaction mixture to form a second reaction mixture including an aminocaproic acid intermediate, performing a separation procedure to have the intermediate separated from the second reaction mixture and performing a hydrogenation procedure to have the aminocaproic acid intermediate hydrogenated to form 6-aminocaproic acid product.

In one embodiment, the acid or base is a base such as alkali metal hydroxide or alkaline earth hydroxide. Specifically, for example, the base is sodium hydroxide or potassium hydroxide. In one embodiment, the acid or base is an acid such as sulfuric acid or hydrochloric acid.

In one embodiment, the water solubility of the aminocaproic acid intermediate is 100 times less than the water solubility of 6-aminocaproic acid, preferably it is less than 200 times.

In one embodiment, the solubility regulating agent is selected from the group consisting of the following: benzyl bromide, 2-chlorobenzyl chloroformate, 4-nitrobenzyl chloroformate, benzyl chloroformate, benzyl (4-nitrophenyl)carbonate, and N-(benzyloxycarbonyloxy)succinimide.

In one embodiment, the aminocaproic acid intermediate is selected from the group consisting of the following: 6-Dibenzylamino-hexanoic acid, 6-(2-Chloro-benzyloxycarbonylamino)-hexanoic acid, 6-(4-Nitro-benzyloxycarbonylamino)-hexanoic acid, 6-Benzyloxycarbonylaminohexanoic acid, 6-Amino-hexanoic acid benzyl ester.

In one embodiment, the hydrolysis procedure is to dissolve ϵ-caprolactam in the acid or base and then heat to reflux for 3~5 hours.

In one embodiment, the modification procedure is to have the solubility regulating agent react with 6-aminocaproic acid in the first reaction mixture to have the solubility regulating agent be bonded to the amino group or carboxylic group of 6-aminocaproic acid.

In one embodiment, the separation procedure is to use an organic solvent to extract the aminocaproic acid intermediate from the second reaction mixture by having the aminocaproic acid intermediate dissolve in the organic solvent to isolate the aminocaproic acid intermediate from aqueous inorganic salt.

In one embodiment, the hydrogenation procedure is to have the aminocaproic acid intermediate react under hydrogen environment at 20~50° C. with existence of hydrogenation catalyst, such as $Pd(OH)_2/C$ or Pd/C.

In one embodiment, residue on ignition of the 6-aminocaproic acid product is less than 0.1 wt % of the 6-aminocaproic product. In one embodiment, heavy metal of the 6-aminocaproic product is less than 0.002 wt %.

Furthermore, one object of the present invention is to provide a 6-aminocaproic acid as an active pharmaceutical ingredient, being formed by the above method according to the present invention.

In one embodiment, residue on ignition of the 6-aminocaproic acid product is less than 0.1 wt % of the 6-aminocaproic product. In one embodiment, heavy metal of the 6-aminocaproic product is less than 0.002 wt %.

In conclusion, according to the method of making 6-aminocaproic acid of the present invention, a 6-aminocaproic product with high purity, low ash content (low salt content), low heavy metal content, low water content, and no odor is provided. Furthermore, this process involves no using of toxic substance such as barium carbonate in the final product. This method uses a low-cost starting material (ϵ-caprolactam) without using column chromatography and it has simple process to be able to massively produce 6-aminocaproic acid to meet the requirements as an active pharmaceutical ingredient.

DESCRIPTION OF THE PREFERRED EMBODIMENTS

What is probed into the invention is a method for making 6-aminocaproic acid. Detail descriptions of the steps and elements will be provided in the following in order to make the invention thoroughly understood. Obviously, the application of the invention is not confined to specific details familiar to those who are skilled in the art. On the other hand, the common steps and elements that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, the method to make 6-aminocaproic acid which comprises: performing a hydrolysis procedure to have ε-caprolactam react with acid or base to generate a first reaction mixture, performing a modification procedure to have a solubility regulating agent react with 6-aminocaproic acid in the first reaction mixture to form a second reaction mixture including an aminocaproic acid intermediate, performing a separation procedure to have the intermediate separated from the second reaction mixture and performing a hydrogenation procedure to have the aminocaproic acid intermediate hydrogenated to form 6-aminocaproic acid product.

Specifically, 6-aminocaproic acid is bonded with the solubility regulating agent to decrease the water solubility. Undesired salts in the reaction mixture can be washed away by water and thus a 6-aminocaproic acid product with low ash content (low salt content) can be obtained.

In this embodiment, the solubility regulating agent is bonded to the 6-aminocaproic acid in the first reaction mixture through the amino group or carboxylic group of 6-aminocaproic acid to form the aminocaproic acid intermediate. Comparing to 6-aminocaproic acid, the water solubility of the aminocaproic acid intermediate is much lower. For example, the water solubility of the aminocaproic acid intermediate is 100 times lower than that of 6-aminocaproic acid. Thus, in this step, 6-aminocaproic acid exists as a form of the aminocaproic acid intermediate, various salts produced during process or reactions can be separated to obtain the aminocaproic acid intermediate with high purity without salt containment. The aminocaproic acid intermediate can be converted into 6-aminocaproic acid through hydrogenation. In one embodiment, the water solubility of the aminocaproic acid intermediate is 100 times less than the water solubility of 6-aminocaproic acid, preferably it is less than 200 times.

In one embodiment, the solubility regulating agent is selected from the group consisting of the following: benzyl bromide, 2-chlorobenzyl chloroformate, 4-nitrobenzyl chloroformate, benzyl chloroformate, benzyl (4-nitrophenyl)carbonate, and N-(benzyloxycarbonyloxy)succinimide.

In one embodiment, the aminocaproic acid intermediate is selected from the group consisting of the following: 6-dibenzylamino-hexanoic acid, 6-(2-chloro-benzyloxycarbonylamino)-hexanoic acid, 6-(4-nitro-benzyloxycarbonylamino)-hexanoic acid, 6-benzyloxycarbonylamino-hexanoic acid, and 6-amino-hexanoic acid benzyl ester. For example, the water solubility of 6-aminocaproic acid is more than 500 mg/ml (6-aminocaproic acid/water) while the water solubility of the above aminocaproic acid intermediate is less than 1.0 mg/ml (aminocaproic acid intermediate/water). Preferably, the aminocaproic acid intermediate is 6-benzyloxycarbonylamino-hexanoic acid.

In one embodiment, the acid or base is a base such as alkali metal hydroxide or alkaline earth hydroxide. Specifically, for example, the base is sodium hydroxide or potassium hydroxide. In one embodiment, the acid or base is an acid such as sulfuric acid or hydrochloric acid.

In one embodiment, the hydrolysis procedure is to dissolve ε-caprolactam in the acid or base and then heat to reflux for 3~5 hours.

In one embodiment, the modification procedure is to have the solubility regulating agent react with 6-aminocaproic acid in the first reaction mixture to have the solubility regulating agent be bonded to the amino group or carboxylic group of 6-aminocaproic acid.

In one embodiment, the separation procedure is to use an organic solvent to extract the aminocaproic acid intermediate from the second reaction mixture by having the aminocaproic acid intermediate dissolve in the organic solvent to isolate the aminocaproic acid intermediate from aqueous inorganic salt.

In one embodiment, the hydrogenation procedure is to have the aminocaproic acid intermediate react under hydrogen environment at 20~50° C. with existence of hydrogenation catalyst, such as Pd(OH)$_2$/C or Pd/C.

In one embodiment, residue on ignition of the 6-aminocaproic acid product is less than 0.1 wt % of the 6-aminocaproic product. In one embodiment, heavy metal of the 6-aminocaproic product is less than 0.002 wt %.

Furthermore, in one embodiment of the invention, a 6-aminocaproic acid as an active pharmaceutical ingredient is provided where the 6-aminocaproic acid is formed by the above method according to the present invention.

In one embodiment, residue on ignition of the 6-aminocaproic acid product is less than 0.1 wt % of the 6-aminocaproic acid product. In one embodiment, heavy metal of the 6-aminocaproic product is less than 0.002 wt %.

EXAMPLE 1

(a) Preparation of 6-dibenzylamino-hexanoic acid

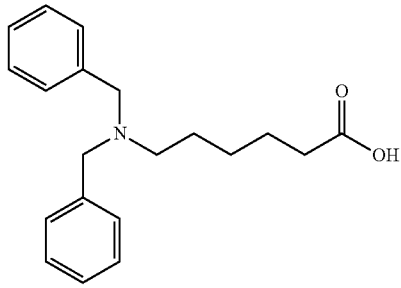 [SMILES: O=C(O)CCCCCN(Cc1ccccc1)Cc1ccccc1]

5 g (44.2 mmol) of ε-caprolactam was dissolved in 23 g of 20 wt % sodium hydroxide solution and the mixture was heated to reflux for 3~5 hours. After hydrolysis of ε-caprolactam was complete, the mixture was cooled to 5~10° C. and then 25 g of tetrahydrofuran was added.

Under 0~5° C., 7.88 ml of benzyl bromide was slowly added into the mixture and the mixture was allowed warm up to room temperature overnight. When the reaction was complete, 20 g of ethyl acetate was added. The aqueous layer was adjusted to pH below than 2 by 16% HCl and extracted with 25 g of ethyl acetate twice. The ethyl acetate layers were collected and then washed with brine. The organic layer was dried by sodium sulfate and concentrated to obtain 7.8 g of 6-dibenzylamino-hexanoic acid. Purity was 95.5%.

(b) Preparation of 6-aminocaproic acid

The concentrate residue was dissolved in 22 g of MeOH and 16 g of water. The mixture was reacted with 0.8 g of Pd(OH)$_2$/C under hydrogen at 50~60 psi at room temperature. When the reaction was complete, Pd(OH)$_2$/C was filtered off and the filtrate was concentrated. The concentrate residue was dissolved in 4 g of water and 16 g of 95% EtOH. 6-aminocaproic acid was crystallized by slowly added 16 g of acetone with stirring and cooling. Repeat the crystallization step to obtain higher than 99.9% purity of aminocaproic acid. Yield was 55.3%.

EXAMPLE 2

(a) Preparation of 6-(2-chloro-benzyloxycarbonylamino)-hexanoic acid

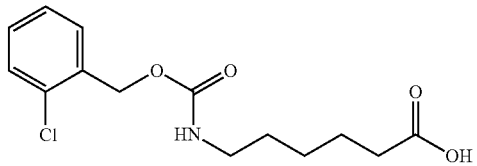 [SMILES: O=C(O)CCCCCNC(=O)OCc1ccccc1Cl]

1 g (8.8 mmol) of ε-caprolactam was dissolved in 3.88 g of 20 wt % NaOH solution and heated to reflux for 3-5 hours. After ε-caprolactam was hydrolyzed completely, the mixture was cooled down to 5~10° C. and 5 g of water was added. 1.8 g (8.8 mmol) of 2-chlorobenzyl chloroformate was added dropwise. The mixture was stirred at room temperature for an hour and washed with 15 g of ethyl acetate twice. The pH of the aqueous layer was adjusted to 1-2 by adding 16% HCl and extracted with ethyl acetate twice. Combined ethyl acetate layer was washed with brine. The organic layer was dried by sodium sulfate and concentrated to obtain 6-(2-Chloro-benzyloxycarbonylamino)-hexanoic acid. Purity was 98.9%.

(b) Preparation of 6-aminocaproic acid

The concentrate residue was dissolved in MeOH and water (3/1 w/w). 10% of Pd(OH)$_2$/C was added. The mixture was reacted at room temperature with hydrogenation at 50-60 psi. When the reaction was complete, Pd(OH)$_2$/C was filtered off and the mixture was concentrated.

The concentrate residue was dissolved in 3.9 g of 95% EtOH. 6-aminocaproic acid was crystallized by slowly added 13 g of acetone with stirring and cooling. Repeat the crystallization step to obtain higher than 99.9% purity of 6-aminocaproic acid.

EXAMPLE 3

(a) Preparation of 6-(4-nitro-benzyloxycarbonylamino)-hexanoic acid

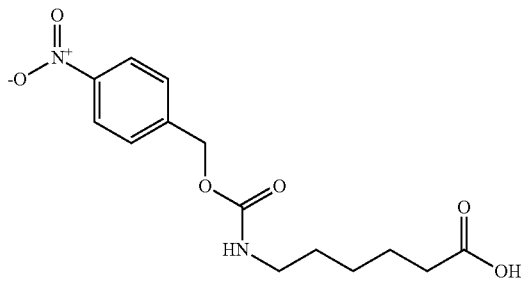

5 g (44.2 mmole) of ε-caprolactam was dissolved in 19.48 g of 20 wt % NaOH and heated to reflux for 3-5 hours. After ε-caprolactam was hydrolyzed completely, the mixture was cooled down to 5~10° C. and then 25 g of water and 10 g of 4-nitrobenzyl chloroformate were added. The mixture was stirred 1 hour at 5-10° C. and then washed with 25 g of ethyl acetate twice. The pH of the aqueous layer was adjusted to 1-2 by adding 16% HCl and extracted with ethyl acetate twice. Combined ethyl acetate layer was washed with water. The organic layer was dried by sodium sulfate and concentrated to obtain 6-(4-nitro-benzyloxycarbonylamino)-hexanoic acid. Purity was 93.9%.

(b) Preparation of 6-aminocaproic acid

The concentrate was dissolved in 140 g of MeOH and 40 g of water. 1.3 g of Pd(OH)$_2$/C was added. The mixture was reacted with hydrogen at 50-60 psi at room temperature. When the reaction was complete, Pd(OH)$_2$/C was filtered and the mixture was then concentrated.

The concentrate residue was dissolved in 30 g of water and washed with 30 g of ethyl acetate. Remove water by vacuum distillation at 45° C. The concentrate residue was dissolved in 12 g of 95% EtOH. 6-aminocaproic acid was crystallized by slowly added 36 g of acetone with stirring and cooling. Repeat the crystallization step to obtain higher than 99.9% purity of 6-aminocaproic acid.

EXAMPLE 4

(a) Preparation of 6-benzyloxycarbonylamino-hexanoic acid

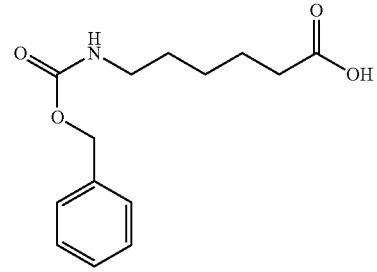 [SMILES: O=C(O)CCCCCNC(=O)OCc1ccccc1]

5 g (44.2 mmol) of ε-caprolactam was dissolved in 19.4 g of 20 wt % NaOH and heated to reflux for 3-5 hours. After ε-caprolactam was hydrolyzed completely, the mixture was cooled down to 5-10° C. and 25 g of benzyl chloroformate was added. The mixture was stirred 1 hour at 5~10° C. and then washed with 25 g of ethyl acetate twice. The pH of the aqueous layer was adjusted to 1-2 by adding 16% HCl and extracted with ethyl acetate twice. Combined ethyl acetate layer was washed with brine. The organic layer was dried by sodium sulfate and concentrated to obtain 6-benzyloxycarbonylamino-hexanoic acid. Purity was 95.0%.

(b) Preparation of 6-aminocaproic acid 12 g of concentrate residue was dissolved in 36 g of MeOH and 24 g of water. 1.2 g of Pd(OH)$_2$/C was added to the mixture and it was reacted at 20-45° C. with hydrogen at 90-100 psi. When the reaction was complete, Pd(OH)$_2$/C was filtered off and the filtrate was concentrated. The concentrate residue was dissolved in 10 g of water and 20 g of 95% EtOH. 6-aminocaproic acid was crystallized by slowly adding 20 g of acetone with stirring and cooling. Repeat the crystallization step to obtain higher than 99.9% purity of 6-aminocaproic acid. Yield was 70.0%.

In another example, benzyl (4-nitrophenyl)carbonate and N-(benzyloxycarbonyloxy)succinimide can be used as the solubility regulating agent instead of benzyl chloroformate in the example 4 and the rest of processing steps and reagents are the same as those of the example 4 to produce 6-aminocaproic acid.

EXAMPLE 5

(a) Preparation of 6-amino-hexanoic acid benzyl ester

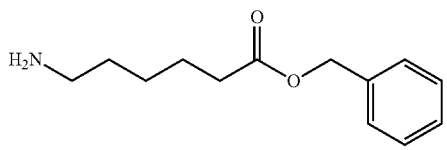 [SMILES: NCCCCCC(=O)OCc1ccccc1]

5 g of ε-caprolactam was dissolved in 10% HCl (20 g) and heated to reflux until the starting material was reacted completely. The pH of the mixture was adjusted to 7.6 by adding 10% NaOH$_{(aq)}$. The mixture was concentrated at 55° C. and then recrystallized in methanol to obtain aminocaproic acid containing inorganic salts.

The mixture (3 g) was added with toluene (30 g), benzyl alcohol (4.45 g) and methanesulfonic acid (2.42 g). The mixture was heated to distill water. When the reaction was complete, the mixture was cooled to 30° C. and added with ethyl acetate (30 g). The organic layer was washed with 5% NaHCO$_3$, brine and dried by sodium sulfate. It was concentrated to obtain 6-amino-hexanoic acid benzyl ester.

(b) Preparation of 6-aminocaproic acid 6.5 g of concentrate residue was dissolved in 20 g of methanol and 13 g of water. 0.6 g of Pd(OH)$_2$/C was added and it was reacted under hydrogen at 50-60 psi. When the reaction was complete, Pd(OH)$_2$/C was filtered off and the filtrate was concentrated. The concentrate residue was dissolved in 30 g of water and washed with 30 g of ethyl acetate. The aqueous layer was concentrated at 45° C. The concentrate residue was dissolved in 10 g of 95% Ethanol. 6-aminocaproic acid was crystallized by slowly adding 10 g of acetone with stirring and cooling. Repeat the crystallization step to obtain higher than 99.9% purity of 6-aminocaproic acid. Yield was 53.8%.

In conclusion, according to the method of making 6-aminocaproic acid of the present invention, a 6-aminocaproic product with high purity, low ash content (low salt content), low heavy metal content, low water content and no odor is provided. Furthermore, the process involves no using of toxic substance. The method uses a low-cost starting material (ε-caprolactam) without using column chromatography in purification and it has simple process to be able to massively produce 6-aminocaproic acid to meet the requirements as an active pharmaceutical ingredient.

Obviously many modifications and variations are possible in light of the above teachings. It is therefore to be understood that within the scope of the appended claims of the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A method of making 6-aminocaproic acid as an active pharmaceutical ingredient, consisting essentially of:
    performing a hydrolysis procedure to have ε-caprolactam react with sodium hydroxide or potassium hydroxide to generate a first reaction mixture and then subsequently performing a modification procedure to have a solubility regulating agent react with the first reaction mixture to form a second reaction mixture including aqueous inorganic salt and aminocaproic acid intermediate;
    performing a separation procedure to have the intermediate separated from the second reaction mixture to use an organic solvent to extract the aminocaproic acid intermediate from the second reaction mixture by having the aminocaproic acid intermediate dissolve in the organic solvent to isolate the aminocaproic acid intermediate from aqueous inorganic salt; and
    performing a hydrogenation procedure to have the aminocaproic acid intermediate hydrogenated to form a 6-aminocaproic acid product;
    wherein the solubility regulating agent is selected from the group consisting of the following: benzyl bromide, 2-chlorobenzyl chloroformate, 4-nitrobenzyl chloroformate, benzyl chloroformate, benzyl (4-nitrophenyl) carbonate, and N-(benzyloxycarbonyloxy)succinimide; and
    aminocaproic acid intermediate is selected from the group consisting of the following: 6-dibenzylamino-hexanoic acid, 6-(2-chloro-benzyloxycarbonylamino)-hexanoic acid, 6-(4-nitro-benzyloxycarbonylamino)-hexanoic acid, and 6-benzyloxycarbonylamino-hexanoic acid.

2. The method according to claim 1, wherein the aminocaproic acid intermediate has water solubility 100 times less than the water solubility of 6-aminocaproic acid.

3. The method according to claim 1, wherein the aminocaproic acid intermediate has water solubility 200 times less than the water solubility of 6-aminocaproic acid.

4. The method according to claim 1, wherein the hydrolysis procedure is to dissolve ε-caprolactam in sodium hydroxide or potassium hydroxide and then heat to reflux for 3~5 hours.

5. The method according to claim 1, wherein the modification procedure is to have the solubility regulating agent react with the first reaction mixture to have the solubility regulating agent be bonded to the amino group.

6. The method according to claim 1, wherein the hydrogenation procedure is to have the aminocaproic acid intermediate react under hydrogen environment at 20~50° C. with existence of hydrogenation catalyst.

7. The method according to claim 1, wherein residue on ignition of the 6-aminocaproic acid product is less than 0.1 wt % of the 6-aminocaproic product.

8. The method according to claim 1, wherein heavy metal of the 6-aminocaproic acid product is less than 0.002 wt % of the 6-aminocaproic acid product.

* * * * *